United States Patent [19]

Villa-Real

[11] Patent Number: 4,492,634
[45] Date of Patent: Jan. 8, 1985

[54] PRE-EVACUATED BLOOD COLLECTION TUBE WITH ANTI-HEMOLYSIS BAFFLE SYSTEM AND CENTRIFUGATION PROPELLED FILTRATION DISC AND EFFICIENT SERUM-FROM CELLS SEPARATOR

[75] Inventor: Antony-Euclid C. Villa-Real, Las Vegas, Nev.

[73] Assignee: EMDE Medical Research, Reno, Nev.

[21] Appl. No.: 434,052

[22] Filed: Sep. 28, 1982

[51] Int. Cl.³ .......................................... B01D 33/00
[52] U.S. Cl. .................................. 210/398; 210/927; 210/516; 210/359; 422/101; 215/247; 128/763; 604/190; 604/230
[58] Field of Search ............... 210/927, 782, DIG. 24, 210/514–518, 359, 305, 306, 398; 422/101; 215/247, 231; 128/760, 763, 764, 765, 766; 604/237, 190, 230

[56] References Cited

U.S. PATENT DOCUMENTS

| 1,737,844 | 12/1929 | Heineman et al. | 604/230 |
| 2,618,264 | 11/1952 | Bloxsom | 604/230 |
| 3,661,265 | 5/1972 | Greenspan | 210/398 X |
| 3,814,248 | 6/1974 | Lawhead | 210/516 |
| 3,848,579 | 11/1974 | Villa-Real | 128/764 |
| 3,881,640 | 5/1975 | Noble | 604/246 |
| 3,897,337 | 7/1975 | Ayres | 210/927 |
| 4,295,476 | 10/1981 | Quaas | 128/764 |

FOREIGN PATENT DOCUMENTS

| 749627 | 4/1970 | Belgium | 215/247 |
| 2824588 | 12/1978 | Fed. Rep. of Germany | 128/764 |

Primary Examiner—Richard V. Fisher
Assistant Examiner—John W. Czaja
Attorney, Agent, or Firm—Young & Martin

[57] ABSTRACT

An improved pre-evacuated blood sampling collection tube having two oppositely positioned rubber stoppers sealing the corresponding oppositely positioned open ends of the said cylindrical tube, and interposed within the said tube is a slideable perpendicularly placed filtration disc that filters and separates the cellular elements of the whole blood from its fluid counterpart during the process of centrifugation. One embodiment of the tube having a special structural extension baffle at one of the two sealing rubber stoppers, said structural extension found proximal to the puncturable entrant area of the blood specimen into the tube, acts as the structural baffle that prevents or curtails hymolysis of the red blood cells during the sudden onrush of blood from the blood source through the bore of the collection needle, and into the vacuum of the said collection tube. Another alternative embodiment comprising of a cylindrical tube with only one open end sealed by a corresponding rubber stopper having a structural extension baffle system, and without an internally located filtration disc.

7 Claims, 17 Drawing Figures

PRE-EVACUATED BLOOD COLLECTION TUBE WITH ANTI-HEMOLYSIS BAFFLE SYSTEM AND CENTRIFUGATION PROPELLED FILTRATION DISC AND EFFICIENT SERUM-FROM CELLS SEPARATOR

BACKGROUND OF THE INVENTION

The present invention relates generally to blood specimen collection tubes, and more particularly to pre-evacuated blood specimen collection tubes provided with a rearward structural extension baffle system that can diminish the occurence of hemolysis or breakdown of fragile red blood cells. It also incorporates in one preferred embodiment the utilization of an internally located filtration disc for the purpose of automatically separating the fluid portion of the blood from the cellular constituents by means of a pre-experimented porous filtration bed that is self-propelled including its ring-like attachment counterpart by the optimal velocity of centrifugal action during the timed centrifugation of the said blood-filled specimen collection tubes.

There are no known devices to date that are capable of attaining the above-mentioned desired performances based on the definite structural make-up of my present invention.

BRIEF SUMMARY OF THE INVENTION

One object of the present invention is to provide an improved disposable pre-evacuated blood collection tube that has an immediate structural baffle extension that can curtail the potential mechanical hemolysis that may result from the high velocity impact of the red blood cells that may strike the far wall of the tube during the sudden onrush of blood from the venous or arterial source through the bore of the cannula and into the inter-connected tube when using the ordinary pre-evacuated tube.

Another object is to provide an improved disposable pre-evacuated tube having two oppositely placed openings with their corresponding sealing rubber stoppers; one opening with its properly installed rubber stopper having the posteriorly located structural baffle extension, said opening being primarily provided for the purpose of the entrance of whole blood from the venous or arterial source, and then later, for the extraction of the separated blood cells after centrifugation; the other opening being sealed with a detachable rubber stopper and said opening which is for the purpose of easy extravtion of serum or plasma from the said tube after proper centrifugation.

Still a further object is to provide an optimally placed filtration disc that is snug-fitting onto the internal wall of the said tube but slideably moveable along the longitudinal axis of the same tube by the propelling force of centrifugal action during the centrifugation process when the filtration disc gradually and automatically filters the whole blood and separates the serum or plasma from the cellular constituents of the same blood specimen.

And yet another object of the present invention is to provide a separator disc which acts as a barrier between the serum or plasma and the cellular constituents of the already properly centrifuged blood specimen so that, during extraction of the serum of plasma protein from one end or the extraction of the cells from the other end for the purpose of laboratory testings, the reasonable manipulative mechanical jarring of disturbances will not any longer intermix the separated serum of plasma with the cellular elements from within the tube.

And yet a further object of the present invention is to provide a separator disc between the already centrifuged serum or plasma portion and the cellular constituents of the blood, so that during transport or handling of the specimen, it is not anymore necessary to maintain the tube in the upright position at all times while the corresponding rubber stoppers are still installed, and, further making it also possible to invert and reverse the upright position of the tube, depending upon the required separated specimen-portion extraction according to the respective laboratory department.

And still another object of the present invention is to provide a centrifugation-propelled filtration disc having a filtration bed with such pre-experimented porosity and inter-webbing structural make-up that, upon the required centrifugation velocity and force, the gradual descent of the filtration disc will not break the cellular elements of the blood while resulting in the clean separation between the serum or plasma portion from the red blood cells and the white blood cells.

DETAILED DESCRIPTIONS OF THE INVENTION

Figure 1:
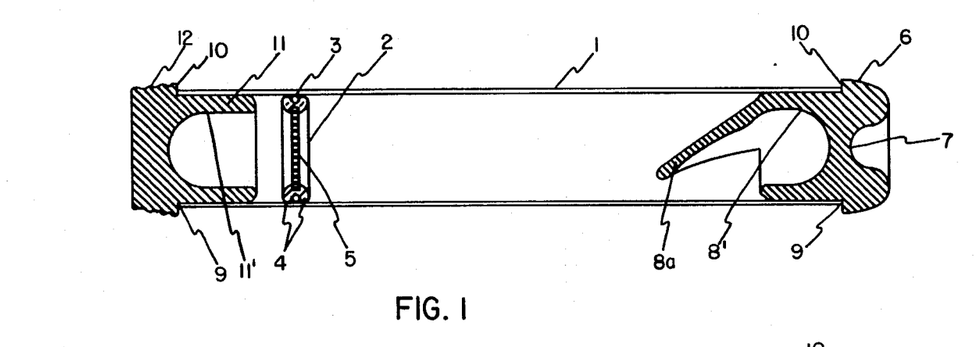
FIG. 1 is an enlarged longitudinal cross-sectional view illustrative of the present invention.
Figure 2:
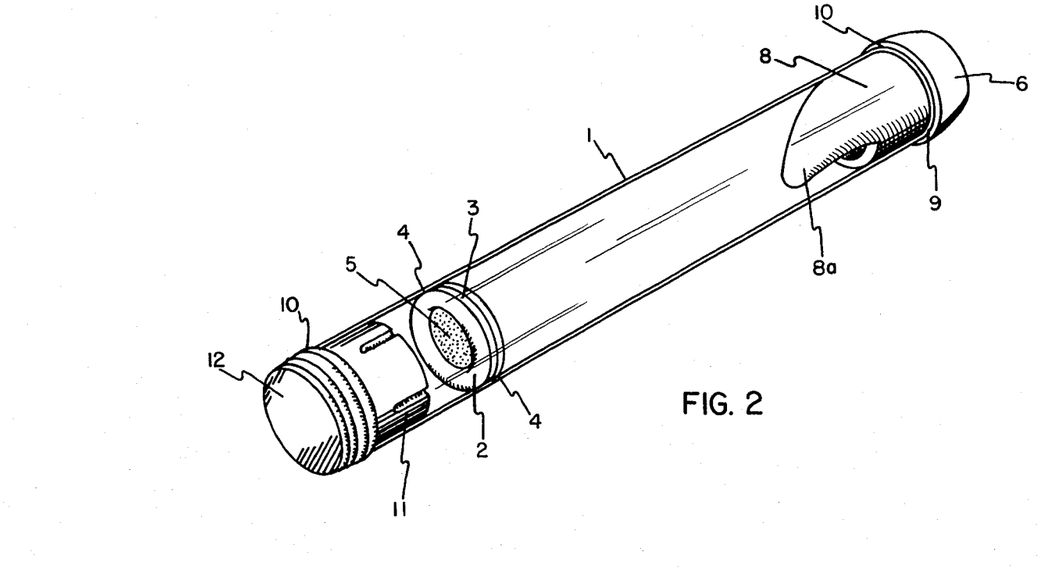
FIG. 2 is an enlarged perspective view of the invention illustrated in FIG. 1.
Figure 3:
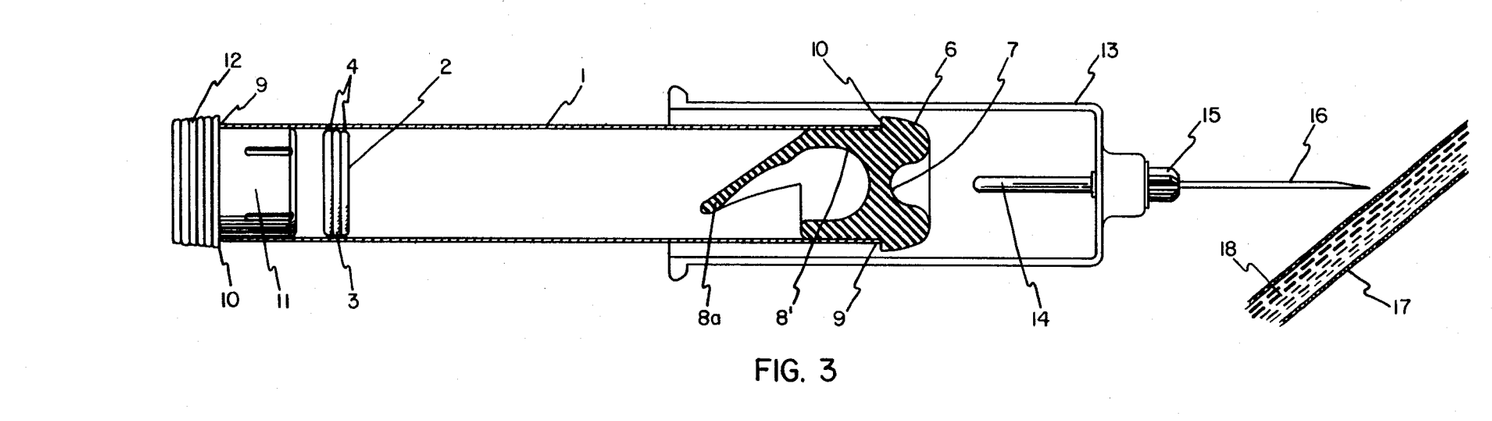
FIG. 3 is an enlarged part side-elevational view of the posterior or rear portion of the device and part-longitudinal cross-sectional view of the anterior or frontal portion, including the tube portion of the same invention as it is mounted in relation to the tube holder before engagement with the current blood sampling collection needle equipped with posteriorly or rearwardly located rubber sleeve, and, showing the frontal portion of the same needle before penetration of the blood vessel.
Figure 4:
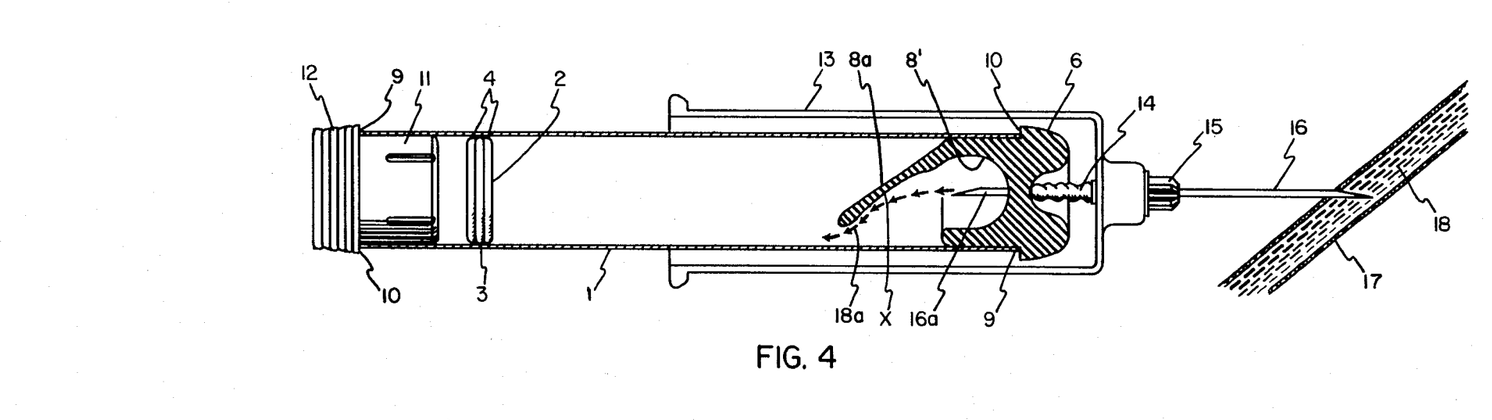
FIG. 4 is an enlarged side-elevational and longitudinal cross-sectional view of the invention illustrated in FIG. 3, only this time the frontal sealing portion of the tube is now engaged with the rear portion of the currently used needle while the frontal portion of the same said needle being now in optimal engagement within the blood vessel.
Figure 5:
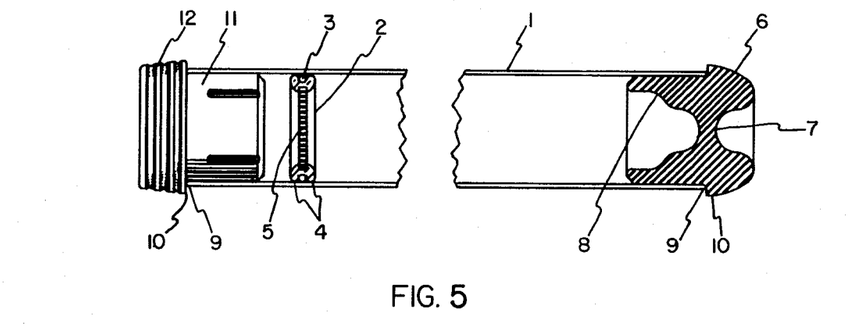
FIG. 5 is an enlarged fragmentary side-elevational view and side-sectional view combination of another alternative type of the invention applicable with my hypodermic needle invention having U.S. Pat. No. 3,848,579.
Figure 6:
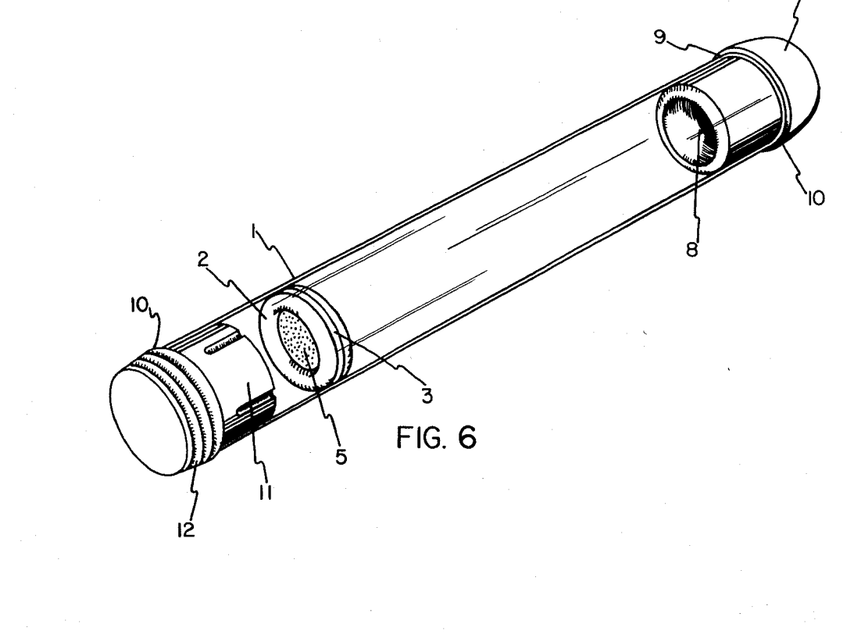
FIG. 6 is an enlarged perspective view of the alternative embodiment of FIG. 5, only that the tube here is shown to be longer.
Figure 7:
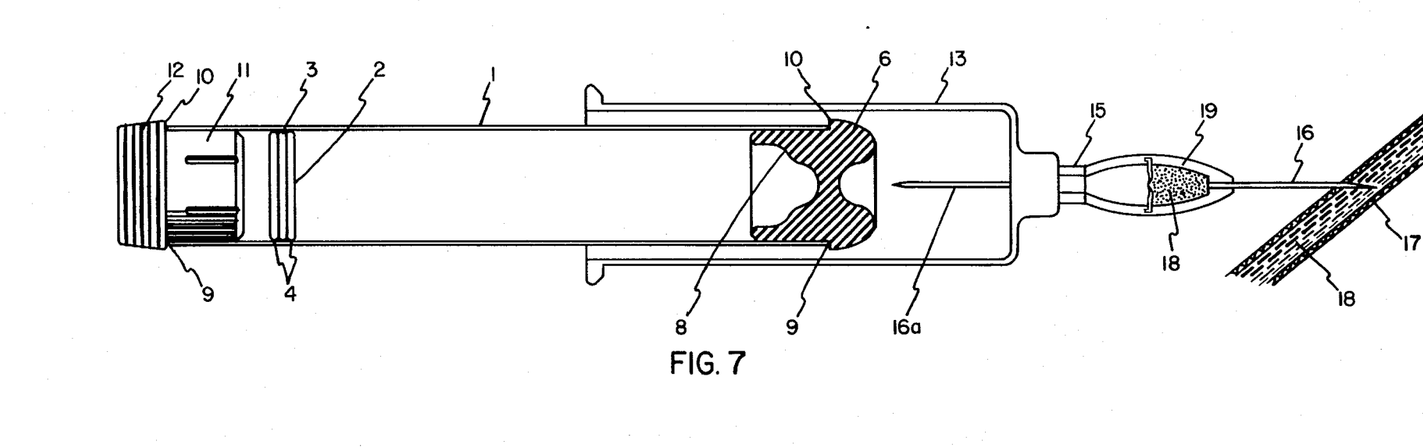
FIG. 7 is an enlarged side-elevational and side-sectional view combination of the embodiment of FIG. 6 whoen as partly engaged within the bore of the tube holder, and shown before the initial phase of puncture by the rear needle portion of my hypodermic needle invention having U.S. Pat. No. 3,848,579, which is illustrated as being properly installed with the tube holder, and, the frontal portion of the same said needle being optimally placed within the lumen of the targeted blood vessel.
Figure 8:
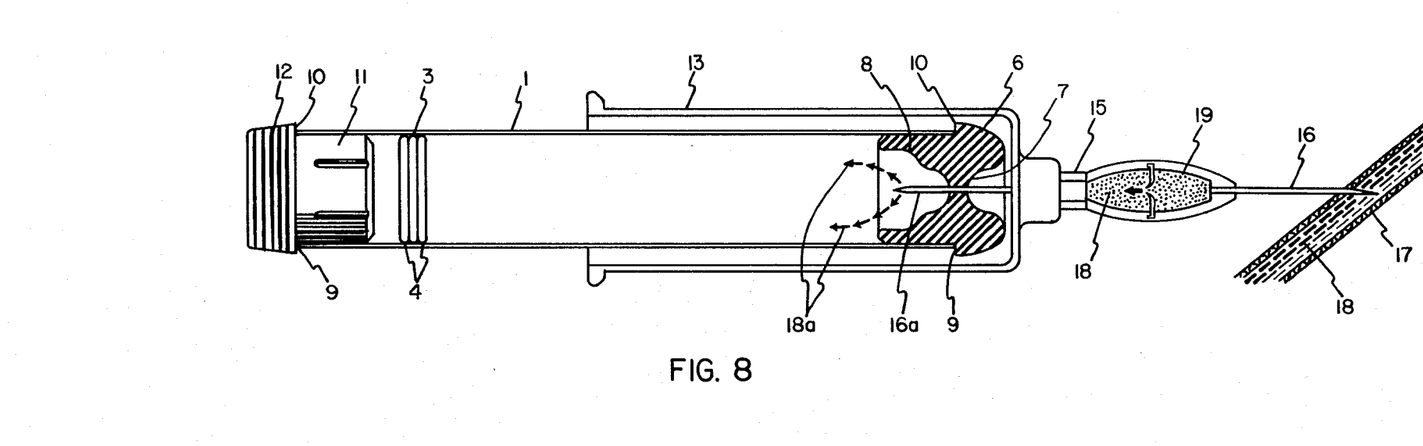
FIG. 8 is an enlarged side-elevational and side-sectional view of the embodiment of FIGS. 5, 6, and 7, and now shown in its puncturing relationship with the hypodermic needle described in FIG. 7.

Referring now to the drawings, wherein like numerals and like numeral-letter combinations refer to like parts, there is shown at FIGS. 1, 2, 3, 4, 5, 6, 7, 8, 9, 10, 11, an improved pre-evacuated blood collection tube 1 having a frontal rubber stopper 6 sealing one of the tubal open ends 9 of the tube, and a rearwardly or posteriorly installed rubber stopper 12 sealing the other open end 9 of the tube. Situated inside the tube is a firm slideable filtration disc 2 that is perpendicularly installed in relation to the longitudinal central axis of the tube which is straight and having circular walls that longitudinally generally run in parallel construction. As can be clearly seen that the filtration disc 2 contains a filtration porous bed 5 which is centrally located and which is primarily used to filter the whole blood sample 18 initially collected into the tube particularly shown in FIG. 9, in order that by the process of centrifugation it is possible to separate the cellular elements 18c of the whole blood from the serum or plasma portion 18b as particulary illustrated in FIGS. 10 and 11. The filtration disc has a generally circularly running outer ridge 4 and also a circularly distributed lubricant and sealant 3 that is chemically inert and which is trapped between the outer circular ridges 4. Circularly running outer ridges 4 of the filtration disc 2 conform with the internal walls of the circular tube 1, and installed in such an optimally slideable but firm relationship to each other, so that, with the aid of the lubricant-sealant 3 trapped within outer ridges 4, it is possible to propel the said filtration disc in a perpendicular manner through the bore of the tube by the force of centrifugal action during the process of centrifugation of the whole blood specimen, so that filtration and separation of the cellular elements of the blood from the fluid portion of the same specimen can be brought about easily by the use of the filtration bed 5 having a porosity range which is pre-calculated in the factory or testing laboratory so as to do the filtration and separation job properly. Numeral 7 is a central depression of rubber stopper 6 designed for the easy puncturing accommodation of the rear portion 16a of the current hypodermic needle 15 installed with tube holder 13 as shown in FIGS. 4 and 8. Numeral 8 is the internal concave portion of rubber stopper 6 and continues structurally to form an extension 8a which acts as a baffle system so that upon entrance of the blood sample 18 being extracted from a venous or arterial source 17 by the front section 16 of the current hypodermic sampling needle 15 having rubber sleeve 14, the high velocity and straight rearward direction of the entering blood into the tube is immediately wedged, deflected, and curtailed as illustrated in FIG. 4 by the arrows 18a thus diminishing the potential hemolysis of the red blood cells during the process of blood extraction into the pre-evacuated blood collection tube.

Figure 17:
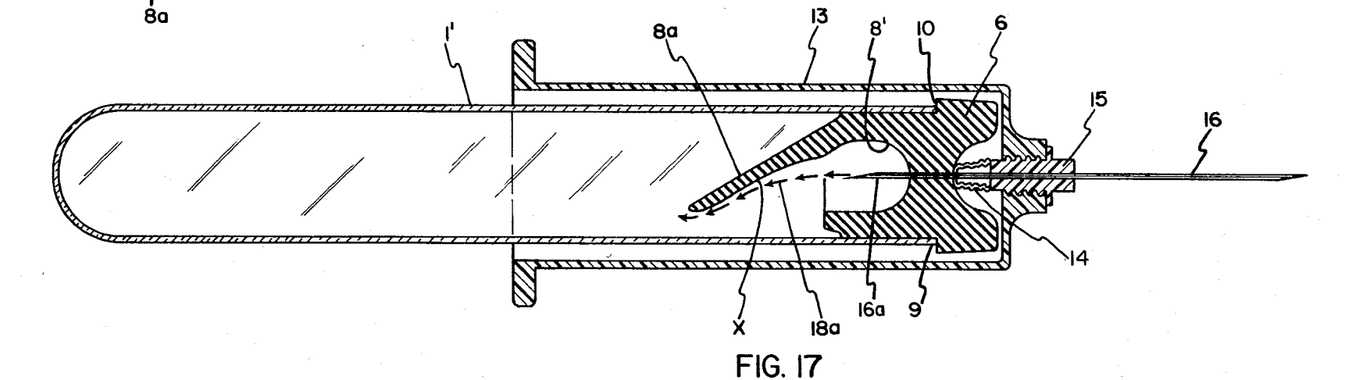
FIG. 17 is a cross-sectional view of an alternative embodiment of a blood collection tube especially adapted to use the rubber stopper of FIG. 16.

The point of impact of the incoming blood from the blood source through the collection needle into the pre-evacuated collection tube is at area X shown in FIGS. 4 and 17. Because of the proximity of the impact point of blood at area X of the structural extension baffle system 8a, in relation to the entrance of the pre-evacuated tube and the rearmost bore of the needle 16a, the ensuing blood that is sucked by the negativity of pressure of the pre-evacuated tube, is not given a chance to gain substantial velocity into the entire length of the tube, because of the immediate deflective action of the baffle extension system 8a. This after-effect illustrates how the curtailment of the potential hemolysis of the fragile red blood cells is brought about. Without the baffle system as in the case of the currently used pre-evacuated tubes in hospitals, laboratories, and doctors' offices, there will be more pre-disposition to hemolysis or breakdown of fragile red blood cells due to the high shear forces to which the blood is exposed as it is sucked across the entire length of the tube and then, after gaining this momentum, is subjected to a higher impact at the internal wall of the tube, initially. This is the chief cause of the falsely high potassium readings due to the release of potassium ions from the hemolyzed red blood cells into the plasma. This is the main reason why the use of the currently applied pre-evacuated tube without the baffle system is not conducive to laboratory chemistry testing especially for the critical chemical analysis of electrolytes involving the potassium level in the plasma or serum.

FIGS. 1, 2, 3, 4, 9, 10, and 17 illustrates the pre-evacuated blood collection tubes specifically for use with the currently utilized blood specimen collection needle having a drip-preventing rubber sleeve (examples of the tubes are those produced by "Becton-Dickinson" or "Terumo").

FIGS. 5, 6, 7, and 8 specifically illustrates the pre-evacuated blood collection tubes that is applicable with my invention having U.S. Pat. No. 3,848,579 entitled "Automatic Elasto-Valvular Hypodermic Sampling Needle" wherein, there is no drip preventing rubber sleeve, but instead, having an automatic controlled elastic valve to prevent the dripping of blood samples during multiple tubular blood sampling. Because of the excellent controlling factor of the elasto-valve in my said previous invention in controlling the sudden onrush of blood into the tube secondary to the pressure differential between the venous or arterial blood source and into the tube, it is therefore not anymore necessary to use the tubes wherein the aforementioned baffle system is incorporated. However, depending upon the medical practitioner or venipuncturist, and also, depending upon the availability, the blood collection tubes having the baffle system can also be used with my aforementioned hypodermic sampling needle invention.

In FIG. 7, the "Automatic Elasto-Valvular Hypodermic Sampling Needle" is shown, wherein the foremost end has already optimally penetrated within the lumen of the blood vessel 17, showing the flowing blood 18, having passed through the front needle 16 and into the front chamber of the transparent needle hub 19. Since the pressure differential between the venous side and the ambient environment is not great enough to open the valve, the blood is not able to cross into the second chamber because the pre-evacuated blood collection tube 1 has not yet been installed with the hind portion 16a of the hypodermic needle.

In FIG. 8, the same "Automatic Elasto-Valvular Hypodermic Sampling Needle" 19 is now in direct communication with the internal section of the pre-evacuated blood collection tube because the rubber stopper of the tube has been already punctured at the depressed area 7 by the rear portion of the pointed needle 16a, showing now the crossing of blood from the first chamber or front chamber of the transparent needle hub into the rear chamber of the same transparent needle hub, through the bore of the rear portion of the needle 16a, and directed into the tube as represented by arrows 18a. Note that the rubber stopper 6 is in engaging relationship with the front edge 9 of the tube 1 by means of lip 10, and that the internal section or wall of the rubber stopper 6 which is represented by numeral 8 does not have a structural extension baffle.

Figure 9:
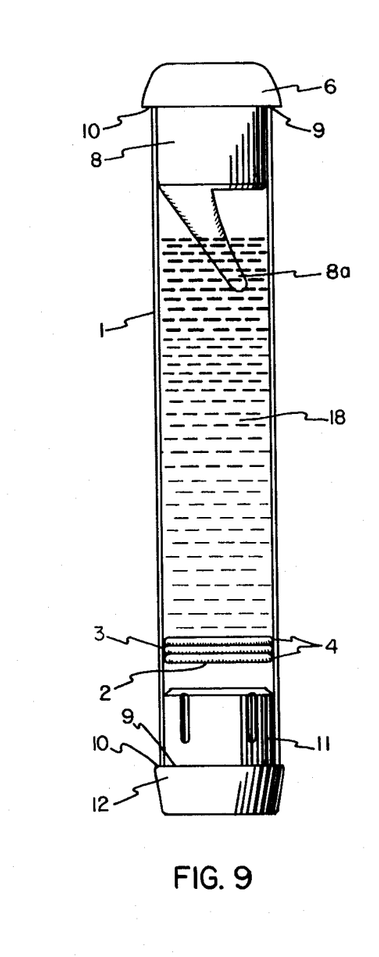
FIG. 9 is an enlarged side-elevational view of the device of FIGS. 1, 2, 3, and 4 and showing the yet unseparated blood collected within the said tube, before the process of centrifugation.

In FIGS. 1, 2, 3, 4, 5, 6, 7, 8, and 9 it is to be noted that the filtration disc is basically situated near the other end of the tube, opposite the end of the tube where entrance of the blood from the source occurs, so that the entering blood being collected within the tube will have enough space to occupy without the structural hindrance of the filtration disc during the course of blood collection, and, during the blood-filled phase of the tube as illustrated in FIG. 9, wherein the collected blood 18 is shown to occupy most of the space up to the proximal border of the filtration disc 2.

Figure 10:
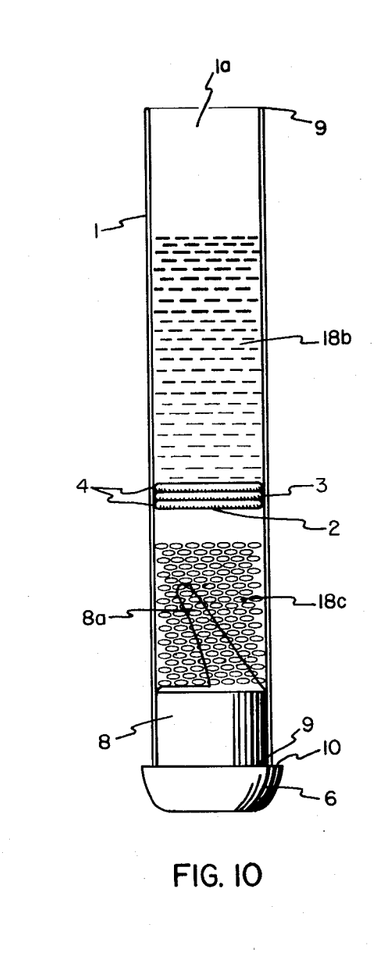
FIG. 10 is an enlarged side-elevational view of the device of FIGS. 1, 2, 3, 4, and 9 wherein one of the rubber stoppers has been removed and showing the filtration disc separating the cellular elements from the fluid portion of the blood after the centrifugation process.

Before the process of centrifugation of the collected blood specimen, the tube is inverted in the centrifuge tube, so that the filtration disc is above the collected blood specimen contained inside the tube. During the process of centrifugation, the centrifugal force generated by the centrifugal action on the centrifuge tube, self-propells the filtration disc downwards, gliding perpendicularly to the bore of the tube, wherein the outer borders 3 and 4 of the filtration disc glides firmly but smoothly against the internal walls of the tube, so that the blood specimen becomes gradually filtered through the filtration velocity of the filtration bed 5 shown specifically by numeral 5 in FIGS. 1, 2, 5, 6, 12, 13, 14, and 15. This process of centrifugation-propelled filtration brings forth the gradual separation of the blood plasma or blood serum that escape through the porous filtration bed 5 of the filtration disc 2, so that toward the end of the process of the optimally timed centrifugation, the serum or plasma that have passed through the porosity of the filtration bed becomes separated from the leftover cellular blood constituents of the collected blood specimen as shown in FIG. 10, wherein the plasma or serum portion 18b of the blood is now separated by the filtration disc 2 from the formed cellular elements 18c of the blood. In this situation, transport of the blood specimen (separated already by centrifugal action, into the fluid portion on one side, and, the cellular elements at the other side) can be safely accomplished from one point of a medical facility to the other, whether the tube is in the perpendicular or horizontal position, without the risk of intermixing again the two separated portions of the blood, as long as the tubes are properly sealed. In FIG. 10, the other rubber stopper 12 of FIG. 9 has already been removed from the corresponding opening of the two-ended opening of the tube, showing in FIG. 10 the exposed opening 1a bordered by 9, thus exposing the filtered fluid portion of the blood ready for clinical laboratory testing such as for chemical analysis of the serum of plasma. The leftover red blood cells and white blood cells including possibly the platelets, all represented by 18c are shown at the bottom of the tube below the filtration disc 2.

Figure 11:
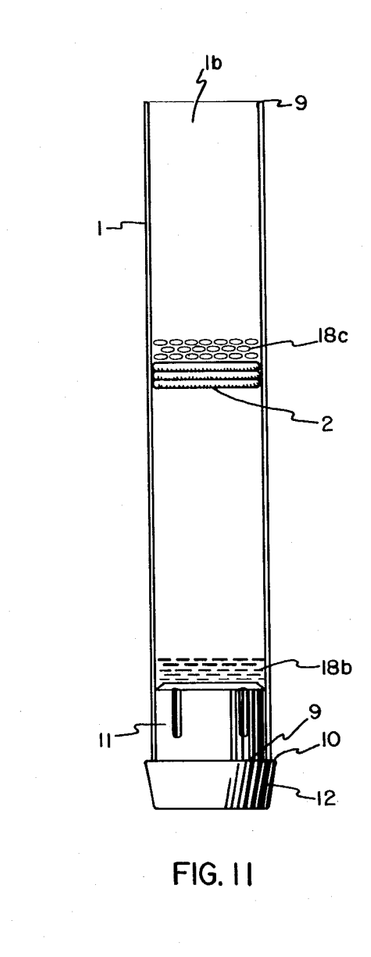
FIG. 11 is an enlarged side-sectional view of the embodiment of FIG. 9, except that, now the tube is in the inverted position as compared to the illustration of FIG. 10, and wherein the cellular elements are now shown on top of the filtration disc, and the fluid portion of the centrifuged blood is now at the bottom of the filtration disc; the rubber stopper that has been removed at FIG. 9 is now shown ot be engaged in the proper sealing relationship at the bottom of the tube; the rubber stopper that is found at the bottom of FIG. 10 has now been removed in this figure.

In FIG. 11, the removed rubber stopper 12 has been engaged back into its sealing position, and then, the tube has been inverted now, so that the leftover serum or plasma portion 18b remains at the bottom of the tube and the filtration disc 2 still separates the cellular elements 18c now found at the upper portion of the tube, above the filtration disc in this position. The rubber stopper 6 shown in FIG. 10 has now been removed exposing the opening 1b bordered by 9, so that red blood cells can easily be accessible to the blood bank technologist or hematologist for the necessary laboratory prodedural testings.

Figure 12:
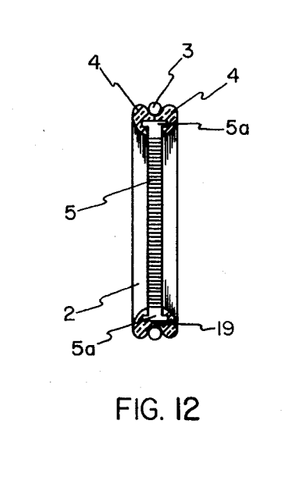
FIG. 12 is an enlarged sectional-view of the filtration disc.
Figure 13:
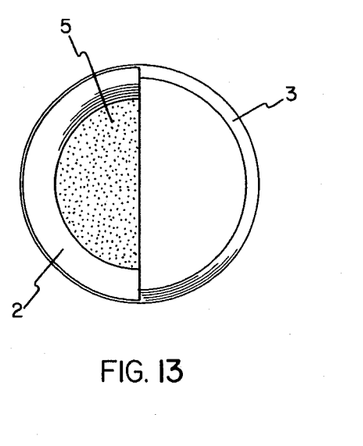
FIG. 13 is an enlarged illustration of the filtration disc of FIG. 12 and partly shown in front view and partly showing the frontal outline of outer borders of the filtration disc.
Figures 14, 15:
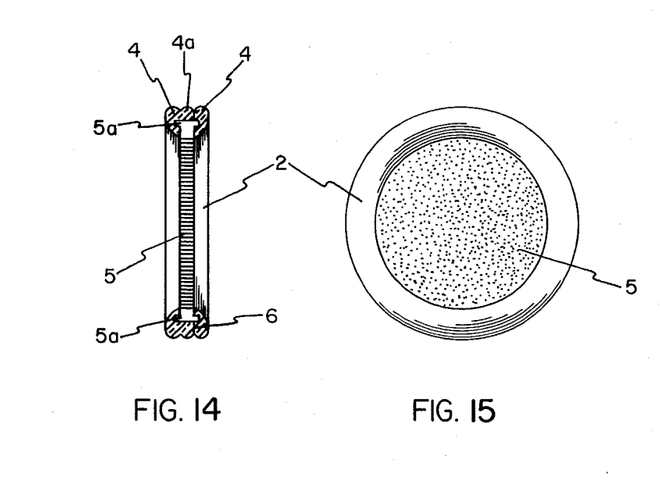
FIG. 14 is an enlarged side-sectional view of another type of filtration disc having parallel triple ridges at its outer periphery.
FIG. 15 is an enlarged front-elevational view of the filtration disc embodiment of FIG. 14.

There are two kinds of filtration discs: One type is fully illustrated in FIGS. 1, 12, and 13, wherein the outer circularly running ridges 4 that run parallel with each other, have a lubricant-sealant 3 found occupying all around the groove between the pair of circularly running ridges 4, and altogether, the engagement of the pair of ridges 4 and the lubricant sealant material found in-between the ridges, act with excellent sliding action against the internal walls of the tube during the process of centrifugal filtration. In FIG. 12, which illustrates this type of filtration disc, the sectional view of the filtration disc 2 reveal clearly the section of the pair of circularly running ridges, and in-between the said ridges is found the sealant-lubricant material 3. The section of the porous filtration bed is also clearly revealed as well as the attachment portion 5a of the filtration bed, situated at the outer boundary and correspondingly engaged in a circularly running complimentary shaped structural groove 19 of the disc structure 2, and, also found near the periphery of the said disc. This structural relationship between the filtration disc and the filtration bed effects an excellent grip upon the filtration bed, so that during the process of centrifugation, the proper filtration can be accomplished without dislodgement of the filtration bed away from its attachment. The other type of filtration disc is illustrated by FIGS. 14 and 15 wherein there is no lubricant-sealant counterpart between the set pair of parallel ridges 4. In place of the lubricant-sealant that occupy the groove between the ridges in FIG. 12, there is a middle circularly running third ridge 4a between the pair of outer circularly running parallel ridges 4. All the other elements are the same as in FIGS. 12 and 13.

Figure 16:
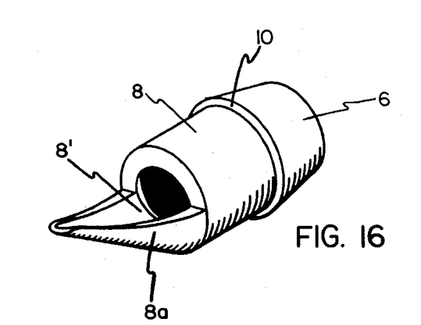
FIG. 16 is a perspective view of an alternative embodiment of a rubber stopper that may be used in this invention.

In FIG. 16, the perspective view of the rubber stopper with a structural extension baffle system is shown wherein the parts are: 8a represents the rearward structural extension baffle system of the rubber stopper 6, 8' is the internal wall of the rubber stopper, 8 represents the outer border of the rubber stopper that is in sealing engagement with the internal wall of the tube, 10 is the circularly running structural border of the rubber stopper that engages in sealing relationship with the circularly running lip or rim of the open end of the tube. FIG. 17 illustrates another alternative embodiment of a pre-evacuated blood collection tube utilizing the type of rubber stopper as in FIG. 16 which contains the rearward structural extension baffle system 8a, however this tube which is cylindrical has only one open end sealed by the said rubber stopper 6 which is now shown in a punctured inter-linking engagement with a currently used hypodermic needle having a rubber sleeve 14 shown in a collapsed manner; said hypodermic needle 15 having a single piece cannular counter-part 16 wherein the rear portion 16a is shown to have penetrated the rubber stopper and now in physical inter-connection with the vacuum of tube 1' which is already sealed by the continuing glass or plastic structure at its rear end. The tube and hypodermic needle holder 13 allows for the proper inter-linking of both the said hypodermic needle and the said tube. This figure also shows the engagement of the rim 9 of the tube that engages against structure 10 of the rubber stopper; also the internal wall 8' of the said rubber stopper is shown as well as the direction of blood flow from the blood source through the cannular bore of the needle and into the tube is represented by the series of rearwardly directed arrows 18a being deflected immediately at point of impact X of the inner wall of the structural extension baffle system 8a.

The invention, as described, is susceptible to modification without departing from the inventive concept and right is herein reserved to such modifications as fall within the scope and equivalence of the appended claims.

What is claimed is:

1. An improved pre-evacuated blood sampling collection tube comprising:

a hollow tube having a first opening located at a first end thereof, a closed second end opposite said first end, and an interior surface;
a detachable first stopper mounted in said first opening, said first stopper including an outer wall adapted to make sealing engagement with said tube interior surface to seal said first opening and a baffle means formed integrally with said outer wall and projecting rearwardly and radially inwardly into said tube for deflecting blood against said interior surface of the tube; and
a filtration disc slideably mounted in said tube for axial motion therealong, said filtration disc oriented perpendicularly to the central axis of said tube and including sealing means thereon for maintaining sealing engagement with said tube interior surface during sliding motion of said filtration disc, said filtration disc operative to separate materials of different physical sizes.

2. A collection tube according to claim 1 wherein said closed second end is defined by a second opening and including a detachable second stopper mounted in said second opening in sealing engagement with said tube interior surface.

3. A collection tube according to claim 2 wherein said first and second stoppers are formed of a rubber-like material.

4. A collection tube according to claim 1 wherein said tube is cylindrical in shape, said filtration disc including an annular member having a central opening and a plurality of spaced-apart outwardly projecting circumferential ridges defining said sealing means and a centrally located porous filtration material extending completely across said central opening, said ridges being in fitting but slideable relationship with said tube interior surface.

5. A collection tube according to claim 4 wherein the region between the ridges contains a chemically inert lubricant.

6. A collection tube according to claim 1 wherein said baffle means comprises a baffle member that is flexible and is generally cup-shaped in configuration and extends from said outer wall through said central axis.

7. A collection tube according to claim 6 wherein said first stopper member has an outwardly opening depression and an inwardly opening concave surface portion each oriented axially thereon to define a portion of reduced cross-section operative to allow puncturing by a hypodermic needle, said baffle member located adjacent said concave surface portion.

* * * * *